United States Patent
Murad et al.

(10) Patent No.: US 9,717,909 B2
(45) Date of Patent: Aug. 1, 2017

(54) SYSTEMS AND METHODS FOR FACILITATING POST-IMPLANT ACOUSTIC-ONLY OPERATION OF AN ELECTRO-ACOUSTIC STIMULATION ("EAS") SOUND PROCESSOR

(71) Applicant: ADVANCED BIONICS AG, Staefa (CH)

(72) Inventors: Carol Murad, Los Angeles, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,029

(22) PCT Filed: Feb. 28, 2014

(86) PCT No.: PCT/US2014/019671
§ 371 (c)(1),
(2) Date: Mar. 22, 2016

(87) PCT Pub. No.: WO2015/130318
PCT Pub. Date: Sep. 3, 2015

(65) Prior Publication Data
US 2016/0235986 A1    Aug. 18, 2016

(51) Int. Cl.
*A61N 1/00*    (2006.01)
*A61N 1/36*    (2006.01)
(Continued)

(52) U.S. Cl.
CPC ....... *A61N 1/36032* (2013.01); *A61N 1/0541* (2013.01); *H04R 25/505* (2013.01); *H04R 25/554* (2013.01); *H04R 25/70* (2013.01)

(58) Field of Classification Search
CPC ............ A61N 1/36032; A61N 1/36014; H04R 25/30; H04R 25/505
See application file for complete search history.

(56) References Cited

U.S. PATENT DOCUMENTS 6,231,604 B1    5/2001    von Ilberg
8,000,798 B2    8/2011    Gantz et al.
(Continued)

FOREIGN PATENT DOCUMENTS

WO    WO-92/08330    5/1992
WO    WO-2005/097255    10/2005
(Continued)

OTHER PUBLICATIONS

International Search Report and Written Opinion received in International Application No. PCT/US14/019671, dated Jun. 17, 2014.

*Primary Examiner* — Robert N Wieland
(74) *Attorney, Agent, or Firm* — ALG Intellectual Property, LLC (57) ABSTRACT

An exemplary system includes 1) an electro-acoustic stimulation ("EAS") sound processor located external to a patient, 2) a cochlear implant communicatively coupled to the EAS sound processor and implanted within the patient, 3) an electrode array communicatively coupled to the cochlear implant and located within a cochlea of the patient, and 4) a receiver communicatively coupled to the EAS sound processor and configured to be in communication with an ear of the patient. The EAS sound processor operates in accordance with an acoustic-only mode during a post-implant time period and detects audio content presented to the patient, directs the receiver to apply acoustic stimulation, and prevents the cochlear implant from applying electrical stimulation representative of audio content presented to the patient during the post-implant time period. Corresponding systems and methods are also disclosed.

20 Claims, 6 Drawing Sheets (51) Int. Cl.
*A61N 1/05* (2006.01)
*H04R 25/00* (2006.01)

(56) References Cited

U.S. PATENT DOCUMENTS

| | | |
|---|---|---|
| 2005/0261748 A1 | 11/2005 | van Dijk |
| 2006/0287690 A1 | 12/2006 | Bouchataoui et al. |
| 2010/0030012 A1 | 2/2010 | Meskens |
| 2013/0345767 A1 | 12/2013 | Menzl et al. |
| 2014/0371623 A1* | 12/2014 | Hong ................ A61B 5/04845 600/559 |

FOREIGN PATENT DOCUMENTS

| | | |
|---|---|---|
| WO | WO-2009/124038 | 10/2009 |
| WO | WO-2013/008057 | 1/2013 |
| WO | WO-2013/115799 | 8/2013 |
| WO | WO-2013/151559 | 10/2013 |

* cited by examiner

SYSTEMS AND METHODS FOR FACILITATING POST-IMPLANT ACOUSTIC-ONLY OPERATION OF AN ELECTRO-ACOUSTIC STIMULATION ("EAS") SOUND PROCESSOR

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

To facilitate electro-acoustic stimulation, a cochlear implant and an electrode array are implanted within a patient as part of a surgical implantation procedure. Following the implantation procedure, the patient is typically required to wait for a period of time (e.g., a few weeks) before the EAS system is turned on to allow the patient to heal from the surgical procedure. Unfortunately, this means that the patient does not benefit from the EAS system during the post-implant waiting period. Moreover, without an enabled EAS system, it is difficult for a clinician to assess or measure how the implantation procedure affected the patient's residual hearing or how the patient's residual hearing progresses during the post-implant waiting period.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for facilitating post-implant acoustic-only operation of an EAS sound processor are described herein. As will be described below, an exemplary system may include 1) an EAS sound processor located external to a patient, 2) a cochlear implant communicatively coupled to the EAS sound processor and implanted within the patient, 3) an electrode array communicatively coupled to the cochlear implant and located within the cochlea of the patient, and 4) a receiver communicatively coupled to the EAS sound processor and configured to be in communication with an ear of the patient. In some examples, the EAS sound processor operates in accordance with an acoustic-only mode during a post-implant time period that begins after implantation of the cochlear implant and electrode array within the patient. For example, the post-implant time period may begin as part of an acoustic fitting procedure that is performed subsequent to (e.g., immediately following) the implantation of the cochlear implant within the patient in which the EAS sound processor is programmed to operate in the acoustic-only mode. As will be described below, the EAS sound processor may operate in accordance with the acoustic-only mode by detecting audio content presented to the patient during the post-implant time period, directing the receiver to apply acoustic stimulation representative of the audio content to the patient during the post-implant time period, and preventing the cochlear implant from applying electrical stimulation representative of the audio content to the patient during the post-implant time period.

The post-implant time period may last for any suitable amount of time (e.g., a few weeks, a month, etc.) that allows the patient to heal from the surgical procedure during which the cochlear implant and electrode array are implanted within the patient. At the end of the post-implant time period, the EAS sound processor may be enabled (e.g., during an electrical fitting procedure) to operate in accordance with an EAS mode. As will be described below, the EAS sound processor may operate in accordance with the EAS mode by detecting audio content presented to the patient subsequent to the post-implant time period, directing the receiver to apply acoustic stimulation representative of a first portion of the audio content to the patient, and directing the cochlear implant to apply electrical stimulation representative of a second portion of the audio content to the patient.

By configuring the EAS sound processor to operate in accordance with the acoustic-only mode following the surgical implantation of the cochlear implant and electrode array, the systems and methods described herein may allow the patient to benefit from the acoustic stimulation functionality of the EAS sound processor while the patient waits for the post-implant time period to elapse. In other words, the systems and methods described herein may enhance the patient's residual hearing soon after (e.g., a few minutes or a few hours after) the surgical implantation procedure while preventing the EAS system from applying electrical stimulation to the patient while the patient heals from the surgical implantation procedure. Moreover, the systems and methods described herein may facilitate assessment of the patient's residual hearing (e.g., how the residual hearing changes following the surgical implantation procedure) while the patient waits for the electrical stimulation functionality of the EAS sound processor to be enabled and/or condition one or more electrodes implanted within the patient's cochlea for electrical stimulation after the post-implant time period elapses.

As used herein, "enhancing" a patient's residual hearing refers to enhancing a functional benefit that the patient receives from his or her residual hearing. Likewise, "assessing" a patient's residual hearing may refer to determining how acoustic stimulation affects the functional benefit that the patient receives from his or her residual hearing.

Figure 1:
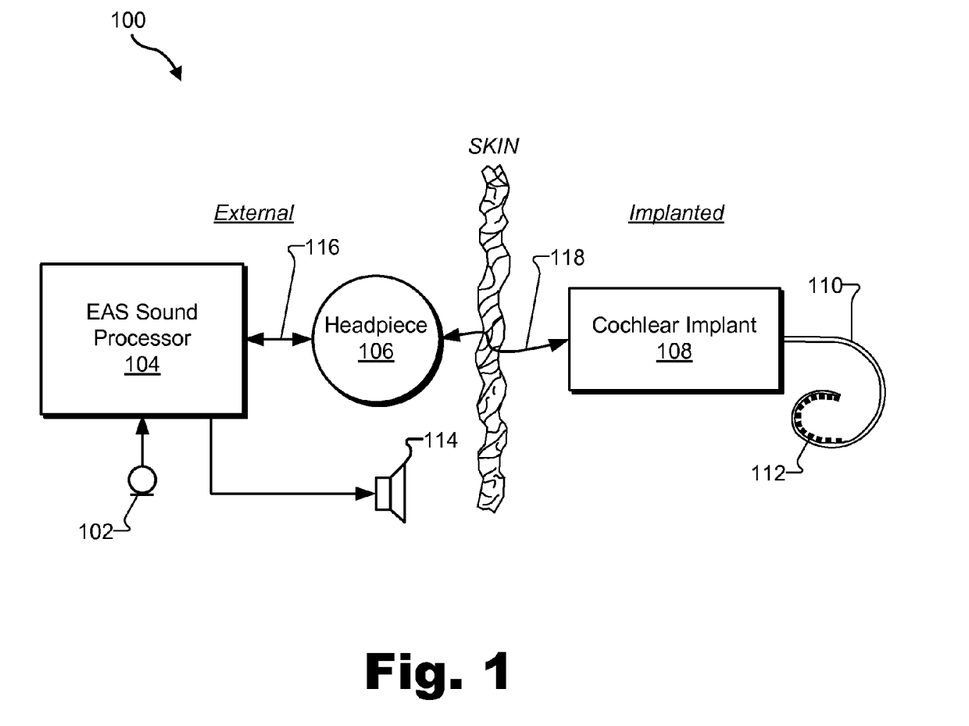
FIG. 1 illustrates an exemplary EAS system according to principles described herein.

FIG. 1 illustrates an exemplary EAS system 100. EAS system 100 may include a microphone 102, an EAS sound processor 104, a headpiece 106 having a coil disposed therein, a cochlear implant 108, an electrode array 110 with a plurality of electrodes 112 disposed thereon, and a receiver 114 (also referred to as a "loudspeaker"). Additional or alternative components may be included within EAS system 100 as may serve a particular implementation.

As shown, various components of EAS system 100 may be located external to the patient including, but not limited to, microphone 102, EAS sound processor 104, headpiece 106, and receiver 114. Various components of EAS system 100 may be implanted within the patient including, but not limited to, cochlear implant 108 and electrode array 110. As will be described in more detail below, additional or alternative components may be included within EAS system 100 as may serve a particular implementation. The components shown in FIG. 1 will now be described in more detail.

Microphone 102 may be configured to detect audio signals (i.e., audio content) presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to EAS sound processor 104. Additionally or alternatively, microphone 102 may be implemented by one or more microphones disposed within headpiece 106, one or more microphones disposed within EAS sound processor 104, and/or any other suitable microphone as may serve a particular implementation.

EAS sound processor 104 (i.e., one or more components included within EAS sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, EAS sound processor 104 may process the one or more audio signals in accordance with a selected sound processing strategy or program to generate appropriate stimulation parameters for controlling cochlear implant 108. EAS sound processor 104 may include or be implemented by a behind-the-ear ("BTE") unit, a body worn device, and/or any other sound processing unit as may serve a particular implementation.

In some examples, EAS sound processor 104 may wirelessly transmit stimulation parameters (e.g., in the form of data words included in a forward telemetry sequence) and/or power signals to cochlear implant 108 by way of a wireless communication link 118 between headpiece 106 and cochlear implant 108. It will be understood that communication link 118 may include a bi-directional communication link and/or one or more dedicated uni-directional communication links.

EAS sound processor 104 may be further configured to direct receiver 114 to apply acoustic stimulation representative of audio content to the patient. This may be performed in any suitable manner.

In some examples, EAS system 100 may be used when the patient has some residual hearing in the low frequencies (e.g., below 1000 Hz) and severe hearing loss in the high frequencies (e.g., above 1000 Hz). To this end, EAS sound processor 104 may direct cochlear implant 108 to apply electrical stimulation representative of audio content included in a relatively high frequency band (e.g., above 1000 Hz) to one or more stimulation sites within the patient (e.g., within the cochlea of the patient) by way of one or more electrodes 112 included in electrode array 110, and receiver 114 to apply acoustic stimulation representative of audio content included in a relatively low frequency band (e.g., below 1000 Hz) to the patient.

Headpiece 106 may be communicatively coupled (e.g., detachably connected) to EAS sound processor 104 by way of a cable 116 and may include an external antenna (e.g., a coil and/or one or more wireless communication components) configured to facilitate selective wireless coupling of EAS sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between EAS sound processor 104 and cochlear implant 108 via a communication link 118 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some examples, cochlear implant 108 may be configured to generate electrical stimulation representative of an audio signal processed by EAS sound processor 104 (e.g., an audio signal detected by microphone 102) in accordance with one or more stimulation parameters transmitted thereto by EAS sound processor 104. To this end, cochlear implant 108 may include one or more current generators.

Cochlear implant 108 may be further configured to apply the electrical stimulation to one or more stimulation sites within the patient via one or more electrodes 112 disposed along electrode array 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
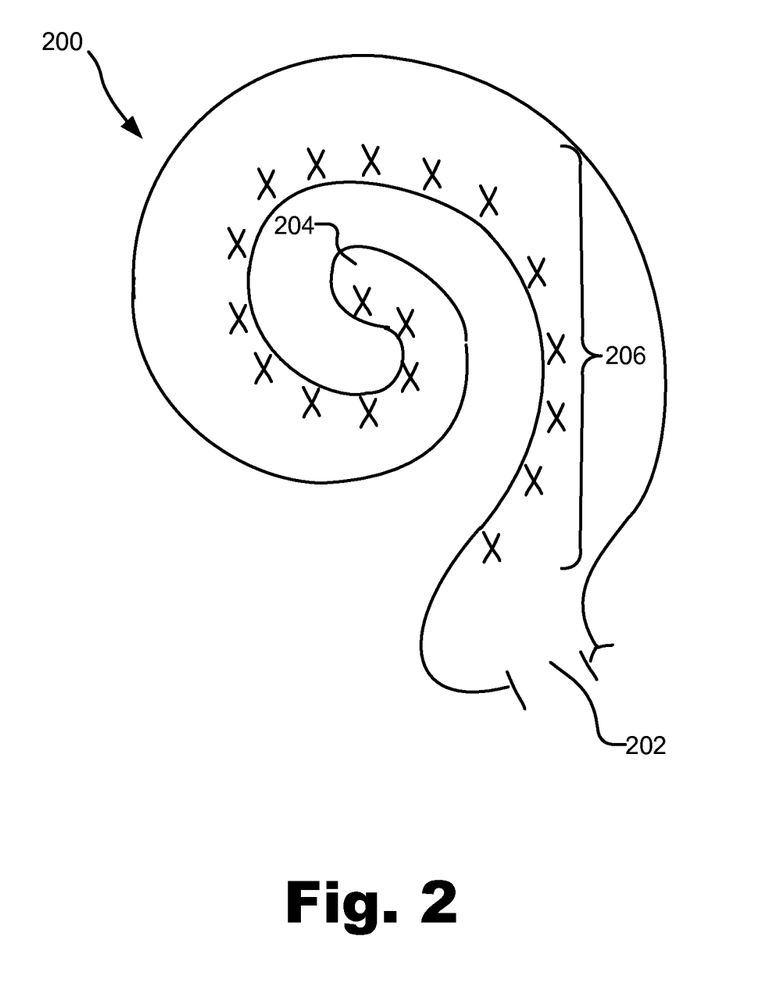
FIG. 2 illustrates a schematic structure of the human cochlea according to principles described herein.

FIG. 2 illustrates a schematic structure of the human cochlea 200 into which electrode array 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Returning to FIG. 1, receiver 114 may be communicatively coupled to EAS sound processor 104 and may be configured to be in communication with an ear of the patient. For example, receiver 114 may be integrated into an earpiece configured to be located within the outer ear of the patient. The earpiece may include any type of earpiece that may be at least partially disposed within the outer ear of the patient. For example, the earpiece may include an open dome configured to allow the ear to remain partially open (e.g., an open dome tip made from a soft silicone material and configured to resemble a tulip or flower bud), a closed dome configured to entirely close off the ear canal, a foam dome, and/or any other type of dome as may serve a particular implementation. As will be described in more detail below, receiver 114 may be configured to apply acoustic stimulation to the patient.

Figure 3:
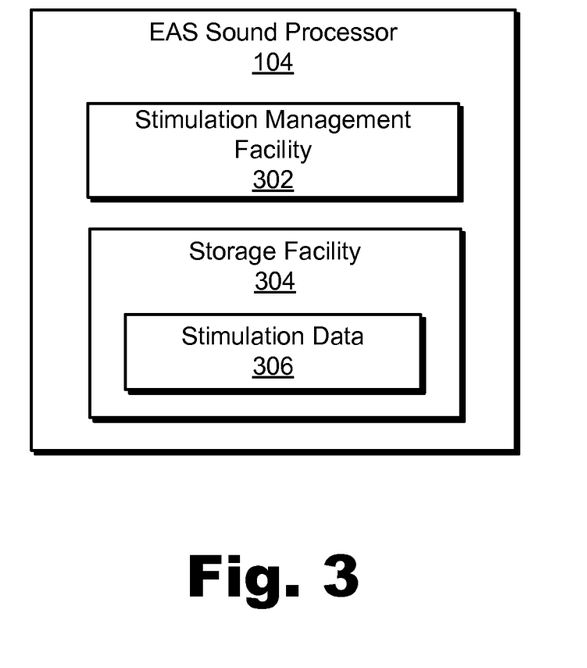
FIG. 3 illustrates exemplary components of an EAS sound processor according to principles described herein.

FIG. 3 illustrates exemplary components of EAS sound processor 104. As shown in FIG. 3, EAS sound processor 104 may include a stimulation management facility 302 and a storage facility 304, which may be in communication with one another using any suitable communication technologies. Storage facility 304 may be configured to maintain stimulation data 306 generated and/or used by stimulation management facility 302. Storage facility 306 may maintain additional or alternative data as may serve a particular implementation. One or more of facilities 302 and 304 may include a computing device or processor configured to perform one or more of the functions described herein.

Stimulation management facility 302 may be configured to perform various stimulation management operations with respect to audio content (e.g., one or more audio signals) presented to a patient. For example, stimulation management facility 302 may receive audio content presented to the patient (e.g., during a normal operation of the EAS system 100). Stimulation management facility 302 may then perform one or more pre-processing operations, spectral analysis operations, noise reduction operations, mapping operations, and/or any other types of processing operations with respect to the received audio content as may serve a particular application. Once the audio content has been processed, stimulation management facility 302 may apply acoustic and/or electrical stimulation representative of the audio content to the patient.

Figure 4:
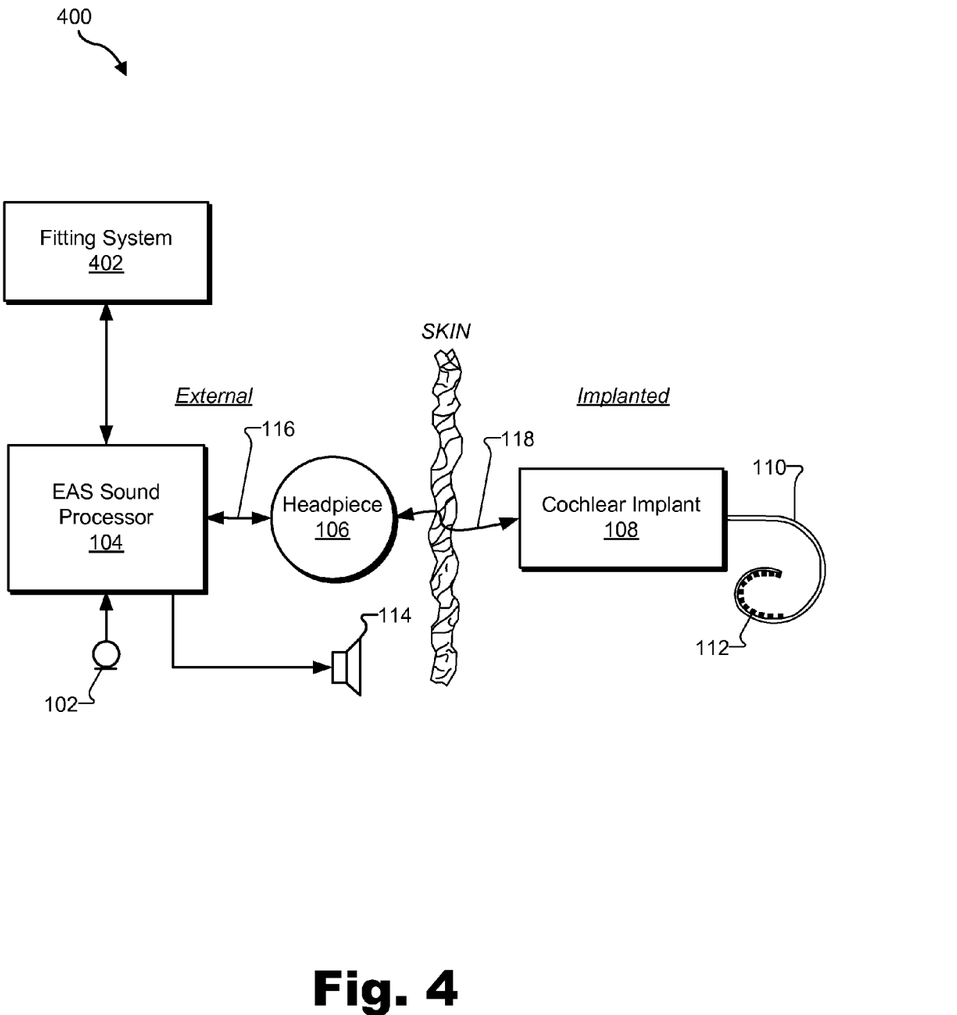
FIG. 4 shows an exemplary configuration in which a fitting system is communicatively coupled to an EAS sound processor according to principles described herein.

FIG. 4 shows an exemplary configuration in which a fitting system 402 is communicatively coupled to EAS sound processor 104. Fitting system 402 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. In some examples, fitting system 402 may provide one or more graphical user interfaces ("GUIs") (e.g., by presenting the one or more GUIs by way of a display screen) with which a clinician or other user may interact.

In some examples, fitting system 402 may be used to perform various types of fitting procedures with respect to EAS sound processor 104. For example, fitting system 402 may be communicatively coupled to the EAS sound processor 104 after (e.g., immediately following) surgical implantation of cochlear implant 108 and electrode array 110 within the patient. While fitting system 402 is communicatively coupled to EAS sound processor 104, fitting system 402 may perform an acoustic fitting procedure in which EAS sound processor 104 is programmed to operate in an acoustic-only mode. This may be performed in any suitable manner. For example, fitting system 402 may program EAS sound processor 104 to operate in the acoustic-only mode by loading an acoustic-only sound processing program onto EAS sound processor 104, enabling (e.g., turning on) an acoustic-only sound processing program already loaded onto EAS sound processor 104, adjusting one or more control parameters associated with EAS sound processor 104, and/or performing any other suitable operation with respect to EAS sound processor 104.

As used herein, EAS sound processor 104 may operate in accordance with an "acoustic-only mode" by only using acoustic stimulation (and not electrical stimulation) to represent audio content presented to the patient. For example, while operating in accordance with the acoustic-only mode, EAS sound processor 104 may detect audio content presented to the patient, direct receiver 114 to apply acoustic stimulation representative of the audio content to the patient, and prevent cochlear implant 108 from applying electrical stimulation representative of the audio content to the patient. EAS sound processor 104 may prevent cochlear implant 108 from applying electrical stimulation representative of audio content in any suitable manner (e.g., by not transmitting instructions to cochlear implant 108 for the cochlear implant 108 to apply electrical stimulation).

Fitting system 402 may also be used to perform an electrical fitting procedure with respect to EAS sound processor 104. For example, fitting system 402 may be again communicatively coupled to the EAS sound processor 104 after the patient has appropriately healed following the surgical implantation of cochlear implant 108 and electrode array 110 within the patient (e.g., a few weeks after the surgical implantation procedure). While fitting system 402 is again communicatively coupled to EAS sound processor 104, fitting system 402 may perform the electrical fitting procedure in which EAS sound processor 104 is programmed to operate in an EAS mode (i.e., a mode in which EAS sound processor 104 may use acoustic and/or electrical stimulation to represent audio content presented to the patient). This may be performed in any suitable manner. For example, fitting system 402 may program EAS sound processor 104 to operate in the EAS mode by enabling an electrical stimulation functionality of the EAS sound processor 104 (e.g., by programming EAS sound processor 104 to direct cochlear implant 108 to apply electrical stimulation representative of audio content to the patient by way of at least one of electrodes 112), loading an EAS sound processing program onto EAS sound processor 104, enabling (e.g., turning on) an EAS sound processing program already loaded onto EAS sound processor 104, adjusting one or more control parameters associated with EAS sound processor 104, and/or performing any other suitable operation with respect to EAS sound processor 104.

Figure 5:
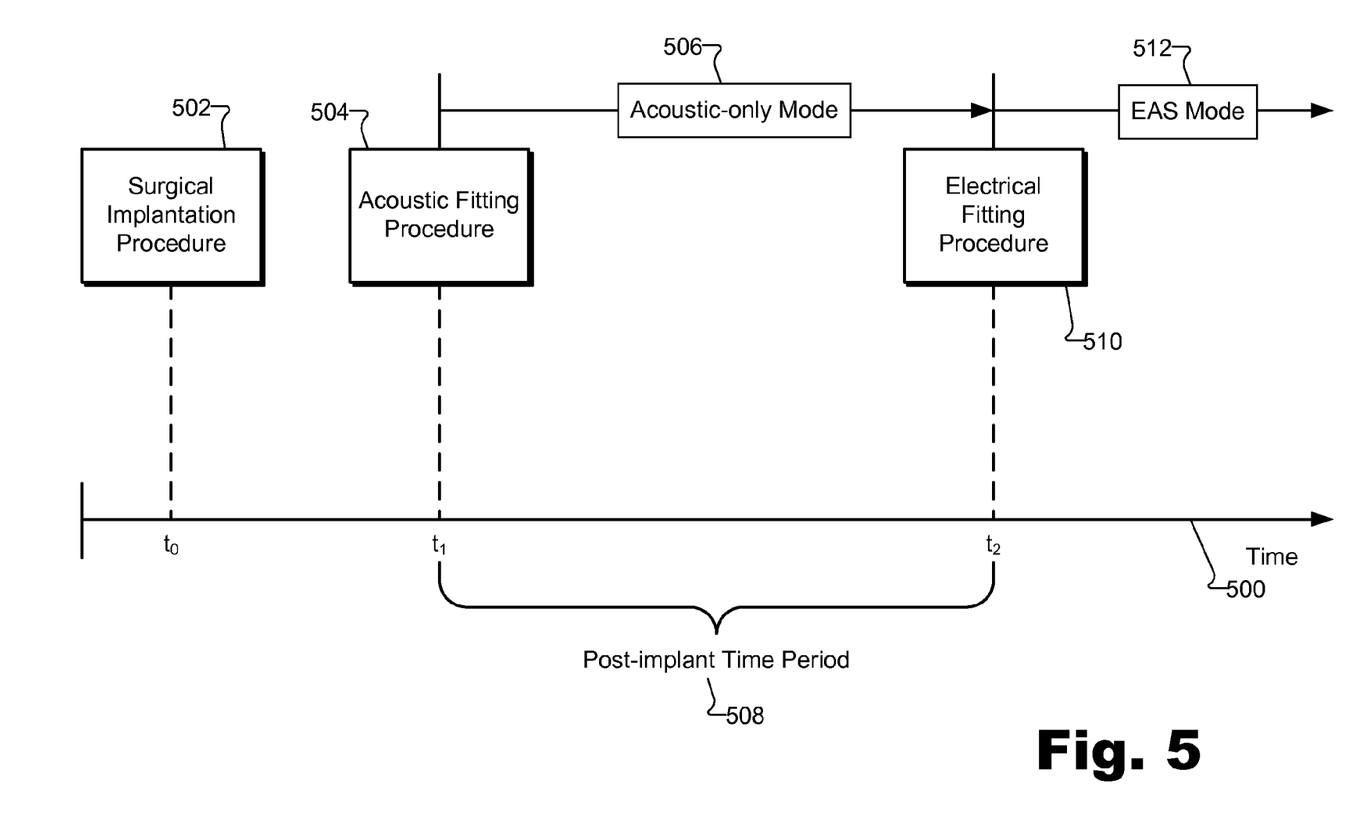
FIG. 5 shows an exemplary timeline associated with a fitting of an EAS system to a patient according to principles described herein.

FIG. 5 shows an exemplary timeline 500 that may be associated with a fitting of EAS system 100 to a patient. As shown in FIG. 5, the timeline begins with a surgical implantation procedure 502 at time t0. The surgical implantation procedure 502 may include a surgeon or other person implanting cochlear implant 108 and electrode array 110 within the patient. Any other suitable components associated with EAS system 100 may be implanted partially or completely within the patient during surgical implantation procedure 502 as may serve a particular implementation.

An acoustic fitting procedure 504 may follow surgical implantation procedure 502 at time $t_1$. The amount of time between surgical implantation procedure 502 and acoustic fitting procedure 504 may be of any suitable duration. For instance, the acoustic fitting procedure 504 may be performed immediately after completion of the surgical implantation procedure 502, a few minutes, days, or hours after completion of the surgical implantation procedure 502. In some instances, the acoustic fitting procedure 504 may be performed before the surgical implantation procedure 502.

During the acoustic fitting procedure 504, EAS sound processor 104 may be programmed to operate in an acoustic-only mode 506. As described above, fitting system 402 may perform acoustic fitting procedure 504. Alternatively, a clinician or other user may perform acoustic fitting procedure 504 (e.g., by interacting directly with EAS sound processor 104).

As shown in FIG. 5, EAS sound processor 104 may operate in accordance with the acoustic-only mode 506 during a post-implant time period 508. Post-implant time period 508 may be of any suitable duration (e.g., a few weeks, a month, etc.) and may commence in response to the acoustic fitting procedure 504 (e.g., at or immediately following time $t_1$). As mentioned previously, while operating during the post-implant time period 508 in accordance with the acoustic-only mode 506, EAS sound processor 104 may apply acoustic stimulation representative of audio content presented to the patient by way of receiver 114 to an ear of the patient and abstain from directing cochlear implant 108 to apply electrical stimulation representative of the audio content.

As shown in FIG. 5, an electrical fitting procedure 510 may be performed towards or at the end of the post-implant time period 508 (i.e., at time $t_2$). During the electrical fitting procedure 510, EAS sound processor 104 may be programmed to operate in an EAS mode 512. As described above, fitting system 402 may perform electrical fitting procedure 510. Alternatively, a clinician or other user may perform electrical fitting procedure 510 (e.g., by interacting directly with EAS sound processor 104).

In some examples, the post-implant time period 508 may complete in response to the electrical fitting procedure 510. Subsequent to the electrical fitting procedure 510, EAS sound processor 104 may operate in accordance with the EAS mode 512. This may occur in any suitable manner. For example, stimulation management facility 302 may detect a completion of post-implant time period 508 and switch to operating in accordance with the EAS mode 512. While operating in accordance with the EAS mode 512, EAS sound processor 104 may detect audio content presented to the patient, direct the receiver 114 to apply acoustic stimulation representative of a first portion of the audio content that is included in an acoustic stimulation frequency range, and direct the cochlear implant 108 to apply electrical stimulation representative of a second portion of the audio content that is included in an electrical stimulation frequency range.

In some alternative examples, EAS sound processor 104 may automatically detect a completion of the post-implant time period 508 by detecting an elapsing of a predetermined amount of time (e.g., 6 weeks). In response, EAS sound processor 104 may automatically switch from operating in accordance with the acoustic-only mode 506 to operating in accordance with the EAS mode 512. In this example, EAS sound processor 104 may be acoustically and electrically fitted prior to the commencement of the post-implant time period. However, the electrical stimulation functionality of the EAS sound processor 104 may be disabled until EAS sound processor 104 detects the elapsing of the predetermined amount of time. To facilitate this automatic switching, EAS sound processor 104 may be configured to track the amount of elapsed time since the acoustic fitting procedure 504 and accordingly switch operating modes when a certain amount of time has elapsed.

While EAS sound processor 104 is operating in accordance with EAS mode 512, an event may occur that prevents cochlear implant 108 from applying electrical stimulation to the patient. For example, the patient may disconnect headpiece 106 from EAS sound processor 104, thereby preventing EAS sound processor 104 from providing electrical stimulation instructions to cochlear implant 108. In some examples, EAS sound processor 104 may detect such an event, and, in response, automatically switch from operating in accordance with the EAS mode 512 to operating in accordance with the acoustic-only mode 506. EAS sound processor 104 may subsequently detect another event that facilitates operation of cochlear implant 108 (e.g., a reconnecting of headpiece 106 to EAS sound processor 104), and, in response, switch back to operating in accordance with the EAS mode 512.

EAS sound processor 104 may switch back and forth between the acoustic-only mode 506 and the EAS mode 512 in any suitable manner. For example, EAS sound processor 104 may switch from operating in accordance with a first sound processing program associated with the acoustic-only mode 506 to operating in accordance with a second sound processing program associated with the EAS mode 512.

In some examples, it may be desirable to apply conditioning electrical stimulation to one or more electrodes 112 disposed within the cochlea of the patient while the EAS sound processor 104 operates in accordance with the acoustic-only mode 506 during the post-implant time period 508. As used herein, "conditioning electrical stimulation" refers to any type of electrical stimulation configured to condition (i.e., maintain patency of or remove biological buildup from) one or more of the electrodes 112 (e.g., one or more apical electrodes) so that the one or more electrodes are available and ready for future standard electrical stimulation (e.g., when EAS sound processor 104 switches to operating in accordance with EAS mode 512).

To this end, headpiece 106 may occasionally be communicatively coupled (e.g., physically connected using cable 116) to EAS sound processor 104 during the post-implant time period 508 (e.g., by the patient and/or by another user). In some examples, EAS sound processor 104 may detect the coupling of headpiece 106 to cochlear implant 108 and, in response, direct cochlear implant 108, by way of headpiece 106, to apply conditioning electrical stimulation to one or more of electrodes 112.

In some examples, the conditioning electrical stimulation may be sub-threshold electrical stimulation that cannot be perceived by the patient. As used herein, "sub-threshold electrical stimulation" includes electrical stimulation that has a stimulation level that is less than a threshold level required for the patient to perceive the electrical stimulation. For example, the conditioning electrical stimulation may include bipolar stimulation (i.e., near-field current stimulation). Bipolar stimulation may be advantageous because relatively high amounts of current may be applied by way of the electrodes before the patient experiences a percept (i.e., before the patient perceives a sound or sensation associated with the application of the bipolar stimulation). Hence, the conditioning electrical stimulation may be applied to one or more of electrodes 112 without the patient being aware of and/or affected by the conditioning electrical stimulation. The conditioning electrical stimulation may additionally or alternatively include monopolar stimulation, multipolar stimulation, and/or any other suitable type of electrical stimulation as may serve a particular implementation.

In some examples, while operating in accordance with acoustic-only mode 506 during the post-implant time period 508, EAS sound processor 104 may evaluate the residual hearing status of a patient and take one or more actions accordingly. A variety of different factors may affect a residual hearing status of a patient. For example, wax buildup in the ear, infection, sickness, patient age, and/or any other factor may temporarily and/or permanently affect a residual hearing status of the patient. Hence, by tracking the residual hearing status of the patient during the post-implant time period 508, changes in the residual hearing status may be accounted for.

EAS sound processor 104 may determine the residual hearing status of the patient in any suitable manner. For example, EAS sound processor 104 may direct cochlear implant 108 and/or receiver 114 to apply stimulation (i.e., electrical stimulation and/or acoustic stimulation) to the patient, record an evoked response that occurs in response to the stimulation, and determine the residual hearing status in accordance with the evoked response. To illustrate, EAS sound processor 104 may compare the evoked response to a baseline response and/or one or more previously recorded evoked responses. As used herein, a "baseline response" refers to some type of fixed evoked response that a clinician may consider to be normal, acceptable, and/or desirable. If the evoked response differs from the baseline response and/or the one or more previously recorded evoked responses (e.g., if the evoked response is not within a predetermined range of the baseline response and/or the one or more previously recorded evoked responses), EAS sound processor 104 (i.e., stimulation management facility 302) may adjust one or more control parameters governing an operation of EAS sound processor 104 and/or cochlear implant 108 (e.g., by increasing an amplitude and/or intensity level of stimulation being provided to the patient), notify the patient (e.g., by way of an audible alert (e.g., one or more beeps), a visible alert (e.g., a flashing of an LED), a text-based alert, and/or any other type of notification as may serve a particular implementation), and/or perform any other action as may serve a particular implementation.

Figure 6:
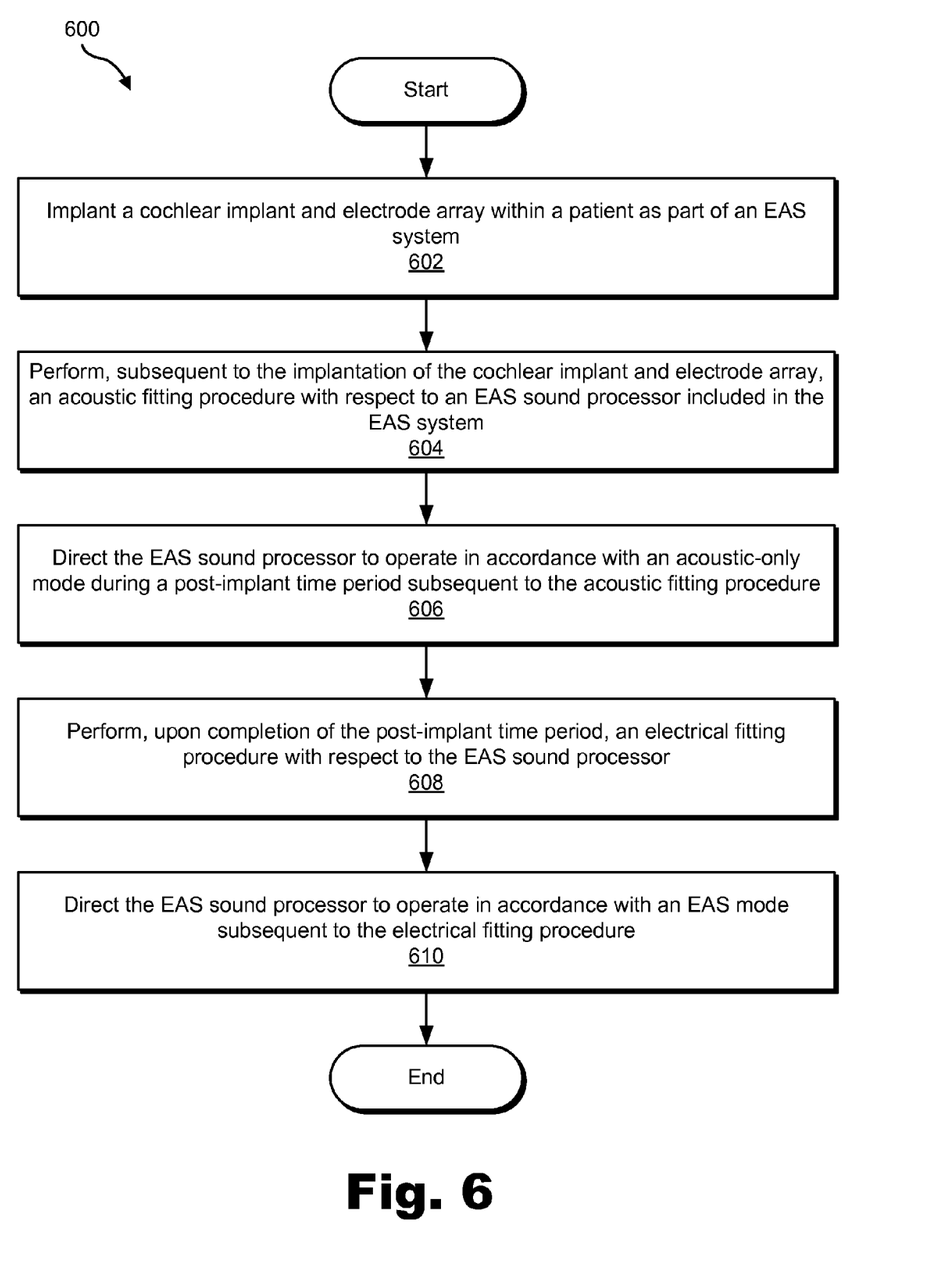
FIG. 6 illustrates an exemplary method according to principles described herein.

FIG. 6 illustrates an exemplary method 600. While FIG. 6 illustrates exemplary steps according to one embodiment, other embodiments may omit, add to, reorder, and/or modify any of the steps shown in FIG. 6. One or more of the steps shown in FIG. 6 may be performed by EAS sound processor 104, fitting system 402, and/or a user (e.g., a surgeon, a clinician, and/or the patient).

In step 602, a cochlear implant and electrode array are implanted within a patient as part of an electro-acoustic stimulation ("EAS") system. Step 602 may be performed in any of the ways described herein.

In step 604, subsequent to the implantation of the cochlear implant and electrode array, an acoustic fitting procedure is performed with respect to an EAS sound processor included in the EAS system. Step 604 may be performed in any of the ways described herein.

In step 606, the EAS sound processor is directed to operate in accordance with an acoustic-only mode during a post-implant time period subsequent to the acoustic fitting procedure. Step 606 may be performed in any of the ways described herein.

In step 608, upon completion of the post-implant time period, an electrical fitting procedure is performed with respect to the EAS sound processor. Step 608 may be performed in any of the ways described herein.

In step 610, the EAS sound processor is directed to operate in accordance with an EAS mode subsequent to the electrical fitting procedure. Step 610 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
an electro-acoustic stimulation ("EAS") sound processor located external to a patient;
a cochlear implant communicatively coupled to the EAS sound processor and implanted within the patient;
an electrode array communicatively coupled to the cochlear implant and located within a cochlea of the patient; and
a receiver communicatively coupled to the EAS sound processor and that is in communication with an ear of the patient;
wherein the EAS sound processor operates in accordance with an acoustic-only mode during a post-implant time period that begins after implantation of the cochlear implant within the patient by
detecting audio content presented to the patient during the post-implant time period,
directing the receiver to apply acoustic stimulation representative of the audio content to the patient during the post-implant time period, and
preventing the cochlear implant from applying electrical stimulation representative of the audio content to the patient during the post-implant time period.

2. The system of claim 1, further comprising:
a fitting system configured to be communicatively coupled to the EAS sound processor and that performs, prior to the beginning of the post-implant time period, an acoustic fitting procedure in which the EAS sound processor is programmed to operate in the acoustic-only mode;
wherein the post-implant time period begins in response to the acoustic fitting procedure.

3. The system of claim 2, wherein the fitting system further performs an electrical fitting procedure in which the EAS sound processor is programmed to direct the cochlear implant to apply electrical stimulation representative of the audio content to the patient by way of at least one electrode included in the electrode array;
wherein the post-implant time period completes in response to the electrical fitting procedure.

4. The system of claim 1, wherein the EAS sound processor:
detects a completion of the post-implant time period; and
switches, in response to the completion of the post-implant time period, to operating in accordance with an EAS mode;
wherein, while operating in accordance with the EAS mode, the EAS sound processor
detects additional audio content presented to the patient subsequent to the post-implant time period,
directs the receiver to apply acoustic stimulation representative of a first portion of the additional audio content to the patient, the first portion included in an acoustic stimulation frequency range, and
directs the cochlear implant to apply electrical stimulation representative of a second portion of the audio content to the patient by way of at least one electrode included in the electrode array, the second portion included in an electrical stimulation frequency range.

5. The system of claim 4, wherein, while the EAS sound processor operates in accordance with the EAS mode, the EAS sound processor:
detects an event that prevents the cochlear implant from applying electrical stimulation representative of the second portion of the audio content; and
in response to the event, automatically switches from operating in the EAS mode to operating in the acoustic-only mode.

6. The system of claim 4, wherein the EAS sound processor detects the completion of the post-implant time period by detecting an elapsing of a predetermined amount of time, and wherein the EAS sound processor automatically switches to operating in accordance with the EAS mode in response to the elapsing of the predetermined amount of time.

7. The system of claim 1, further comprising:
a headpiece configured to be communicatively coupled to the EAS sound processor by way of a cable and that facilitates wireless communication between the EAS sound processor and the cochlear implant;
wherein the EAS sound processor, during the post-implant time period,
detects a coupling of the headpiece to the EAS sound processor, and
directs, by way of the headpiece while the headpiece is coupled to the EAS sound processor, the cochlear implant to apply conditioning electrical stimulation to one or more electrodes included in the electrode array.

8. The system of claim 7, wherein the conditioning electrical stimulation is sub-threshold electrical stimulation that cannot be perceived by the patient.

9. The system of claim 1, wherein, while the EAS sound processor operates in accordance with the acoustic-only mode, the EAS sound processor:
evaluates a residual hearing status of the patient; and
adjusts one or more control parameters associated with the EAS sound processor in accordance with the evaluated residual hearing status.

10. The system of claim 9, wherein the EAS sound processor evaluates the residual hearing status of the patient by:
directing at least one of the cochlear implant and the receiver to apply stimulation to the patient,
recording an evoked response that occurs in response to the stimulation, and
determining the residual hearing status in accordance with the evoked response.

11. A system comprising:
an electro-acoustic stimulation ("EAS") sound processor located external to a patient;
a cochlear implant communicatively coupled to the EAS sound processor and implanted within the patient;
an electrode array communicatively coupled to the cochlear implant and located within a cochlea of the patient;
a receiver communicatively coupled to the EAS sound processor and that is in communication with an ear of the patient;
a headpiece configured to be communicatively coupled to the EAS sound processor by way of a cable and that facilitates wireless communication between the EAS sound processor and the cochlear implant;
wherein the EAS sound processor operates in accordance with an acoustic-only mode during a post-implant time period that begins after implantation of the cochlear implant within the patient by
directing the receiver to apply acoustic stimulation representative of audio content presented to the patient during the post-implant time period,
preventing the cochlear implant from applying electrical stimulation representative of the audio content presented to the patient during the post-implant time period; and
wherein, during the post-implant time period, the EAS sound processor
detects a coupling of the headpiece to the EAS sound processor, and
directs, in response to the coupling of the headpiece to the EAS sound processor, the cochlear implant by way of the headpiece to apply conditioning electrical stimulation to at least one electrode included in the electrode array.

12. The system of claim 11, further comprising:
an acoustic fitting system configured to be communicatively coupled to the EAS sound processor and that performs, prior to the beginning of the post-implant time period, an acoustic fitting procedure in which the EAS sound processor is programmed to operate in the acoustic-only mode;
wherein the post-implant time period begins in response to the acoustic fitting procedure.

13. The system of claim 11, wherein the conditioning electrical stimulation is sub-threshold stimulation that cannot be detected by the patient.

14. The system of claim 11, wherein, while the EAS sound processor operates in accordance with the acoustic-only mode, the EAS sound processor:
evaluates a residual hearing status of the patient; and
adjusts one or more control parameters associated with the EAS sound processor in accordance with the evaluated residual hearing status.

15. The system of claim 14, wherein the EAS sound processor evaluates the residual hearing status of the patient by:
directing at least one of the cochlear implant and the receiver to apply stimulation to the patient,
recording an evoked response that occurs in response to the stimulation, and determining the residual hearing status in accordance with the evoked response.

16. The system of claim 11, further comprising:
an electrical fitting system configured to be communicatively coupled to the EAS sound processor and that performs an electrical fitting procedure in which the EAS sound processor is programmed to direct the cochlear implant to apply electrical stimulation representative of the audio content to the patient by way of at least one electrode included in the electrode array;
wherein the post-implant time period completes in response to the electrical fitting procedure.

17. The system of claim 11, wherein the EAS sound processor:
detects a completion of the post-implant time period; and
switches, in response to the completion of the post-implant time period, to operating in accordance with an EAS mode;
wherein, while operating in accordance with the EAS mode, the EAS sound processor
detects additional audio content presented to the patient subsequent to the post-implant time period,
directs the receiver to apply acoustic stimulation representative of a first portion of the additional audio content to the patient, the first portion included in an acoustic stimulation frequency range, and
directs the cochlear implant to apply electrical stimulation representative of a second portion of the audio content to the patient by way of at least one electrode included in the electrode array, the second portion included in an electrical stimulation frequency range.

18. The system of claim 17, wherein the EAS sound processor detects the completion of the post-implant time period by detecting an elapsing of a predetermined amount of time, and wherein the EAS sound processor automatically switches to operating in accordance with the EAS mode in response to the elapsing of the predetermined amount of time.

19. The system of claim 17, wherein, while the EAS sound processor operates in accordance with the EAS mode, the EAS sound processor:
detects an event that prevents the cochlear implant from applying electrical stimulation representative of the second portion of the audio content; and
in response to the event, automatically switches from operating in the EAS mode to operating in the acoustic-only mode.

20. A method comprising:
implanting a cochlear implant and electrode array within a patient as part of an electro-acoustic stimulation ("EAS") system;
performing, subsequent to the implanting, an acoustic fitting procedure with respect to an EAS sound processor included in the EAS system;
directing the EAS sound processor to operate in accordance with an acoustic-only mode during a post-implant time period subsequent to the acoustic fitting procedure;
performing, upon completion of the post-implant time period, an electrical fitting procedure with respect to the EAS sound processor; and
directing the EAS sound processor to operate in accordance with an EAS mode subsequent to the electrical fitting procedure.

\* \* \* \* \*